(12) United States Patent  
Feitisch et al.

(10) Patent No.: US 10,024,788 B2  
(45) Date of Patent: Jul. 17, 2018

(54) SPECTROMETER WITH RANDOM BEAM PROFILES

(71) Applicant: SpectraSensors, Inc., Rancho Cucamonga, CA (US)

(72) Inventors: Alfred Feitisch, Los Gatos, CA (US); Peter Dorn, Rancho Cucamonga, CA (US); James Tedesco, Ann Arbor, MI (US); Xiang Liu, Rancho Cucamonga, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/703,616

(22) Filed: May 4, 2015

(65) Prior Publication Data

US 2016/0327479 A1    Nov. 10, 2016

(51) Int. Cl.

| | |
|---|---|
| *G01J 3/28* | (2006.01) |
| *G01N 21/39* | (2006.01) |
| *G01N 21/3504* | (2014.01) |
| *G01N 21/03* | (2006.01) |
| *G01J 3/02* | (2006.01) |

(52) U.S. Cl.  
CPC ............ *G01N 21/39* (2013.01); *G01J 3/0208* (2013.01); *G01N 21/031* (2013.01); *G01N 21/3504* (2013.01); *G01N 2021/399* (2013.01); *G01N 2201/0612* (2013.01); *G01N 2201/0633* (2013.01)

(58) Field of Classification Search  
CPC .... G01N 21/39; G01J 3/02; G01J 3/10; G01J 3/28  
See application file for complete search history.

(56) References Cited

U.S. PATENT DOCUMENTS

| 5,929,981 | A | * | 7/1999 | Keilbach | ................ | G01N 21/15 |
|---|---|---|---|---|---|---|
| | | | | | | 356/301 |
| 6,064,488 | A | | 5/2000 | Brand et al. | | |
| 7,679,059 | B2 | | 3/2010 | Zhou | | |
| 9,518,866 | B2 | | 12/2016 | Feitisch et al. | | |
| 9,816,860 | B2 | | 11/2017 | Feitisch et al. | | |

(Continued)

FOREIGN PATENT DOCUMENTS

| DE | 19840345 A1 | 3/2000 |
|---|---|---|
| EP | 0203767 A2 | 12/1986 |
| WO | WO-2004/113887 A2 | 12/2004 |

OTHER PUBLICATIONS

Herriott, D., Kogelnik, H., and Kompfner, R. "Off-Axis Paths in Spherical Mirror Interferometers." *Applied Optics*, vol. 3, No. 4, 1964, pp. 523-526.

(Continued)

*Primary Examiner* — Abdullahi Nur  
(74) *Attorney, Agent, or Firm* — Mintz Levin Cohn Ferris Glovsky and Popeo, P.C.

(57) ABSTRACT

A spectrometer includes a light source configured to emit a beam along a beam path through a sample volume comprising an analyte. Also included is at least one detector positioned to detect at least a portion of the beam emitted by the light source, and at least one reflector positioned along the beam path intermediate the light source and the at least one detector having a surface roughness greater than a predefined level such as 20 Å RMS.

43 Claims, 4 Drawing Sheets

(56) References Cited

U.S. PATENT DOCUMENTS

| | | |
|---|---|---|
| 2003/0094433 A1* | 5/2003 | Ouellet .............. G02B 5/0891 |
| | | 216/24 |
| 2003/0190113 A1 | 10/2003 | Huang et al. |
| 2005/0128403 A1* | 6/2005 | Liu .................. G02F 1/134363 |
| | | 349/141 |
| 2005/0129840 A1 | 6/2005 | Lee et al. |
| 2005/0213092 A1 | 9/2005 | MacKinnon et al. |
| 2005/0229698 A1 | 10/2005 | Beecroft et al. |
| 2008/0239306 A1 | 10/2008 | Sutherland et al. |
| 2011/0066092 A1 | 3/2011 | Moeskops et al. |
| 2011/0140870 A1 | 6/2011 | Ullrich |
| 2011/0164251 A1* | 7/2011 | Richter .............. G01N 21/031 |
| | | 356/440 |
| 2011/0239421 A1 | 10/2011 | Tertitski et al. |
| 2011/0299076 A1 | 12/2011 | Feitisch et al. |
| 2013/0077097 A1 | 3/2013 | Engstrand |
| 2014/0160474 A1 | 6/2014 | Keller et al. |
| 2014/0168649 A1 | 6/2014 | Smith |
| 2016/0066775 A1 | 3/2016 | Hunter et al. |

OTHER PUBLICATIONS

Herriott, Donald R. and Schulte, Harry J. "Folded Optical Delay Lines." *Applied Optics*, vol. 5, No. 8, 1965, pp. 883-889.

* cited by examiner

SPECTROMETER WITH RANDOM BEAM PROFILES

TECHNICAL FIELD

The subject matter described herein relates to spectroscopic analyzers in which a beam emitted by a light source passes through a sample cell in which beam profile and collimation are being modified by non-optimal conditions (e.g., through diffraction, refraction, scattering, absorption, optical interference, etc.) and which, nonetheless, yields meaningful data regarding an analyte in a sample in the cell. Also described herein are systems for spectroscopic analysis that include imperfect light sources.

BACKGROUND

Spectrometry techniques can be used to identify the presence of a target chemical species, or analyte, in a gas sample. Spectrometry techniques commonly rely on the interaction of the analyte with light, either in the visible spectrum or at wavelengths that cannot be seen. Depending on the spectrometry technique used, the spectra collected may show the intensity of light absorbed, light emitted, or light scattered from a sample after an exciting beam of light passes through the gas sample. Peaks or dips in the spectral profile of the received light intensity can be indicative of particular chemical species. In some spectrometry techniques, quantities or relative amounts of each chemical species can be derived from the spectra. However, if insufficient amounts of light from the gas sample are collected by a spectrometer, then the spectra may yield no useful data, or can result in noisy data. Noisy data can be inconclusive and meaningful information can be difficult to obtain from such data.

Variations in environmental conditions, aging or fouling of reflector surfaces in a spectrometer sample cell, or replacement of fouled or deteriorated reflector surfaces can cause a beam path of a light and/or a beam profile of a light and/or intensity of a light from a light source within a spectrometer to change. The change can occur over time or as a result of changing a reflector. Changes of the beam path in an optical spectrometer can reduce the amount of light available for analysis from the sample cell. Furthermore, changes of a beam path can cause an offset from calibration of the spectrometer, especially for optical absorption spectroscopy, where absorption of light follows the Beer-Lambert law $$\left(T = \frac{I}{I_0} = e^{-\Sigma l} = e^{-\sigma l N} \text{ or } A = -\ln\left(\frac{I}{I_0}\right)\right),$$

scaling exponentially with path length. Changing or repairing the sample cell in a spectrometer can require calibration or alignment of spectrometry system by a skilled technician. Such service calls and factory repairs are costly and result in downtime for the spectrometer and the operation it controls.

SUMMARY

In one aspect, an apparatus, such as a spectrometer, includes a light source configured to emit a beam along a beam path through a sample volume comprising an analyte. Also included is at least one detector positioned to detect at least a portion of the beam emitted by the light source, and at least one reflector positioned along the beam path intermediate the light source and the at least one reflector having a surface roughness greater than about 20 Å RMS.

In some variations, there can be at least one aperture included along the beam path between light source and detector.

The at least one reflector can be integral to a housing of a sample cell (i.e., the reflector can be a wall of the housing, etc.). In other variations, the at least one reflector can be coupled to a housing of a sample cell.

The at least one reflector can have a radius of curvature varying from a predetermined radius of curvature by more than ±0.05%, ±0.075%, ±0.1%, ±0.15%, ±0.22%, ±0.5%, ±1%, ±1.5%, or ±2%. The predetermined radius of curvature can be based, for example, on a spacing and position of the at least one reflector in relation to the at least one light source and/or at least one detector. The predetermined radius of curvature can be based on the design considerations of applying the sample cell reflector configuration as a laser resonator in which optical losses from diffraction are substantially eliminated or minimized to being close to being eliminated (one can specify approximately <1% power loss in the beam due to diffraction). Alternatively, the predetermined radius of curvature of the sample cell reflectors can be based upon design rules for optical delay lines, which materially preserve transmitted light power, beamshape and wavefront of the light beam traversing the sample cell (D. R. Herriott and H. J. Schulte. *Applied Optics* August 1965, vol. 4, no. 8, p. 883 and D. R. Herriott, H. Kogelnik and R. Kompfner. *Applied Optics* 1964, vol. 3 no. 4, p. 523).

At least a portion of the at least one reflector can have a radius of curvature that is infinite or substantially infinite. At least a portion of the at least one reflector can have a negative radius of curvature. At least a portion of the at least one reflector can have a positive radius of curvature. The at least one reflector can be a cylindrical reflector. The at least one reflector can be an aspheric reflector. The at least one reflector can be a toroidal reflector with a closed ring shape in polar direction and at least one of a spherical shape, of a parabolic shape, of an elliptical shape, of an aspheric shape or the like in the direction perpendicular to the ring. At least a portion of the at least one reflector can be cylindrical, aspheric, toroidal, spherical, parabolic or elliptical.

The at least one reflector can have, for example, a surface roughness greater than 20 Å RMS, 40 Å RMS, 80 Å RMS, 100 Å RMS, 150 Å RMS, 200 Å RMS, 250 Å RMS, 500 Å RMS, or 1000 Å RMS over at least a surface area of, for example, 10 μm by 10 μm.

The at least one reflector can have a surface figure greater than, in at least one area, λ/100, λ/50, λ/10, λ/5, λ/2λ, 2λ, 3, 5, or 10.

The one or more reflective surfaces can cause a loss of intensity of the beam from the light source to the at least one detector. The one or more reflective surfaces can randomly diffract the beam from the light source. The one or more reflective surfaces can diffract the beam from the light source in a predetermined pattern.

The one or more reflective surfaces can cause scattering, diffractive, or both scattering and diffractive signal losses such that an intensity of the beam detected by the at least one detector is below a predefined percentage of an intensity of the beam as emitted by the light source.

The one or more reflective surfaces can comprise single point diamond turned mirrors. The one or more reflective surfaces can comprise molded mirrors. The one or more reflective surfaces can comprise cold formed mirrors. The one or more reflective surfaces can comprise pressed and sintered mirrors. The one or more reflective surfaces can comprise dry or wet etched mirrors. The one or more reflective surfaces can comprise a glass material, a ceramic material, a metal, a plastic material, a dielectric material, a semiconductor or any combination thereof. The one or more reflective surfaces can comprise a glass material, a ceramic material, a metal, a semiconductor, or a plastic material coated with a metal or a dielectric or a semiconductor.

In an interrelated aspect, a light source forming part of a spectrometer, emits a beam along a beam path into a sample volume comprising an analyte. Thereafter, at least one detector detects at least a portion of the beam emitted by the light source after the beam has been reflected by at least one reflector. The at least one reflector is positioned along the beam path intermediate the light source and the at least one detector and has a surface roughness greater than about 20 Å RMS. Subsequently, a concentration of the analyte is calculated based on an intensity level of the detected at least a portion of the beam.

The subject matter described herein provides many technical and cost advantages. For example, a spectrometry system may yield meaningful information despite using lower cost reflectors and other optical elements, which deviate materially from the ideal, finely polished optical surfaces with tight radius of curvature and tight surface figure tolerances, which can be derived from a well understood Gaussian beam propagation analysis of a sample cell with at least one reflection. Furthermore, degradation of spectrometer light transmission due to age and environmental factors or due to reflector exchanges would retain spectrometer calibration fidelity by analyzing data based upon the total power of light, at a wavelength, which is non-resonant with the at least one absorbing gas species in the sample, simultaneously or near simultaneously with the signal of a second- or higher-order harmonic frequency light generated by absorption from the light after passing through the gas sample. Ratioing the total non-resonantly transmitted power with the 2f signal generated by the target analyte absorption, will provide a correct concentration value for the target analyte regardless of any changes in total light transmission, which are not caused by the absorbing target analyte. Alternatively, a possible calibration offset with respect to the time of calibration, which may be caused by a change in light transmission of the spectrometry system, due to reflector exchanges, aging, environmental conditions or fouling from the gas sample and the like, can be compensated by analyzing a light transmission of the spectroscopy system without absorption in the gas sample. This may be achieved by changing the wavelength to coincide with a non-absorptive region of the sample gas or by operating the sample cell with zero gas, which does not absorb light at or close to a wavelength of interest for a target analyte.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. It should be noted that the current subject matter contemplates both a closed sample cell and an open path system for detecting trace gases and/or liquids. The terms "sample gas volume", "gas volume", "sample liquid volume" and "liquid volume" as used herein therefore refers to either a flowing volume or a static, batch volume of gas or liquid (as the case may be).

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
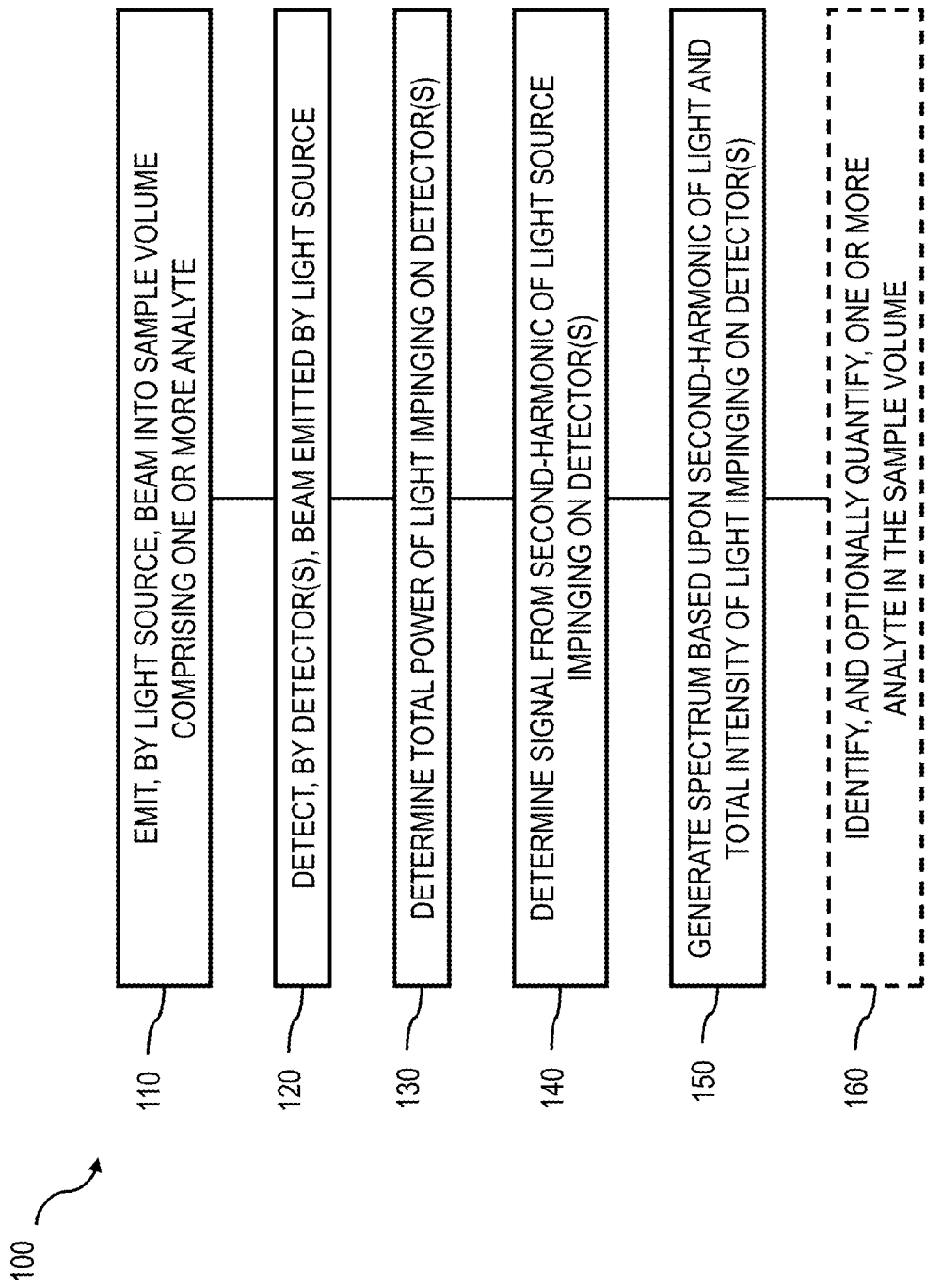
FIG. 1 is a process flow diagram illustrating acquisition and analysis of spectroscopic data from a gas sample.

Spectrometers and spectrometry systems used in laboratories often utilize sample cells having precisely manufactured components (referred to herein sometimes as "ideal" sample cells). Ideal sample cells can include Herriot cells, White cells, and other sample cells with optically optimized reflective surfaces and cell dimensions to yield minimal losses and long path lengths for the light beam passing through the analysis sample. An ideal sample cell used in a laboratory setting can be cleaned before each use, and the spectrometry system can be aligned and calibrated frequently. Spectrometers and spectrometry systems with ideal sample cells, particularly those that are cleaned and aligned frequently, can have a long path length with little deterioration in the beam, resulting in a high intensity of light that passes through a gas sample in the sample cell, and in turn a good signal and data for analysis.

In contrast, industrial settings often do not allow for the downtime to clean and calibrate a spectrometer, particularly to maintain the spectrometer's sample cell. Additionally, sample cells can be exposed to harsh environments that can damage or foul surfaces when used in an industrial setting. This damage or fouling can lead to reduction of the intensity of light that is available for analysis after passing through a gas sample in the sample cell. In turn, the reduced light intensity can lead to deterioration in the data quality.

The spectrometers, spectroscopic systems, and methods described herein can utilize TDL (tunable diode laser)

spectrometers that can require a factory calibration of the sample cell when at least one reflector in the cell is replaced due to fouling or due to other deterioration of a reflecting surface. The factory turn-around time and the cost of such a sample cell repair and replacement has precluded TDL spectrometers from being used in many petrochemical production processes. For example, in ethylene and propylene production and other petrochemical processes, unavoidable reactor upset conditions can result in liquids flowing through sample cells and in leaving damaging residue on reflectors which can make design of a robust spectrometry analysis system with limited down-time challenging and/or excessively expensive.

TDL absorption spectrometers can employ the Beer-Lambert law to quantify the concentration of an absorbing species in a sample gas by quantifying the transmitted light intensity at a chosen wavelength where a target analyte absorbs. The concentration of an absorbing analyte can be derived directly from the transmitted light intensity by integrating the spectral intensity of the transmitted light over a spectral profile of the chosen absorption feature or by fitting of a spectral absorption profile of the transmitted light to a theoretical spectral absorption mode or to a database of measured absorption profiles. This approach is generally referred to as direct absorption spectroscopy (DAS).

An alternate absorption spectroscopy approach can include modulating the transmitted light wavelength sinusoidally while scanning the light wavelength across a chosen analyte absorption feature. Analyte concentrations can be derived from evaluating the spectral intensity profile of the transmitted light received by a detector, at a multiple of the sinusoidal modulation frequency of the light beam transmitted through the sample gas. This approach is generally referred to as wavelength modulation spectroscopy (WMS). TDL absorption spectrometers can employ detection at the $2^{nd}$ harmonic (2f) of the sinusoidal wavelength modulation, also referred to as 2f-WMS. Higher order harmonic frequencies of the sinusoidal wavelength modulation of the transmitted light beam can also be used for concentration quantification, without limitations to the order of the harmonic frequency.

It will be appreciated that absorption spectrometers need to be calibrated against sample gas standards with known concentrations of a desired target analyte, under controlled conditions. The calibration can optionally be traceable to NIST or other national standards organizations. It will also be appreciated that such calibration can incorporate the total transmitted direct and/or harmonic light intensity received by the detector of an absorption spectrometer and that such transmitted light beam intensity received by the detector of an absorption spectrometer can be a result of any combination of the following: absorption, scattering, diffraction, refraction, and beam shape distortion on reflective surfaces, for example reflective surfaces on and/or inside transmissive optical elements in the light beam path passing through the sample cell from the emitting light source to the detector. Furthermore, the light intensity received by the detector can depend upon at least one of absorption, scattering, refraction, diffraction, beam shape distortions caused by the sample cell and the optical system, and the beam path length in the sample gas. Especially a change of a beam path length in the sample gas influences the concentration calculation of a target analyte exponentially, as per the Beer-Lambert law.

Maintaining long-term concentration measurement fidelity of a target analyte by an absorption spectrometer, with respect to a factory calibration, is critically important for industrial process and/or quality and or safety and/or environmental emissions control applications. Repeated field calibration of an absorption spectrometer may be highly undesirable and/or impossible due to being time consuming, costly and causing downtime for the operation controlled by or monitored by the absorption spectrometer. In many cases, suitable calibration gas mixes may not be available in transportable form or at remote locations.

In an attempt to support such requirements, TDL spectrometers as provided herein can follow optical design approaches for shaping and routing of collimated laser beams, which are well understood and can be numerically calculated and practiced by those skilled in the art of routing collimated laser beams with minimal optical losses and/or distortion of a Gaussian beam profile. This can require utilizing expensive transmissive and reflective optical elements, which have been manufactured to small tolerances of any combination of: surface figure of <approximately $\lambda/100$; radius of curvature variation of <±0.016% in relation to a predefined/desired radius of curvature (e.g., the ideal ROC as defined by the required spacing of the reflectors in relation to the light source, etc.); and polished surface roughness (below approximately 20 Angstrom RMS), which can minimize at least one of the following: light scatter, absorption, transmission losses, diffraction, and refraction.

A very long absorption path length in a sample gas of a TDL spectrometer can be achieved by using a Herriott cell, a White cell, a Pfund cell optical configuration, or the like, which involves multiple reflections of a laser beam, which can reimage the beam such that the beam spot sizes on the reflectors remain invariant. The design rules and mathematical equations for such optically non-resonant, long-path length optical systems, that maximize light transmission of Gaussian laser beams, are well understood, since the 1960s, and are therefore being applied to TDL spectrometer absorption sample cell construction by those skilled in the art of optical design.

As an example, a commercially available SpectraSensors TDL analyzer for control of $H_2S$ in natural gas, to below the 4 ppmv government mandated tariff level, uses a Herriott cell with an approximately 28 m path length and approximately 10% of the light beam intensity from the emitting light source reaching the detector at time of factory calibration, after approximately 70 reflections of the light beam on spherical mirrors with approximately 40 cm radius of curvature. As an example, to satisfy the conditions of such a Herriott cell, as mathematically described by D. Herriott, K. Kompfer "Off-Axis Paths in Spherical Mirror Interferometers" Applied Optics Vol. 3, No. 4 (1964); D. Herriott and D. J. Schulte in their 1965 publication "Folded Optical Delay Lines," mirrors need to be manufactured to the following, tight tolerances of less than approximately ±0.016% variation for ROC (radius of curvature) and better than $\lambda/100$ surface figure, where $\lambda$ is the wavelength of the reflected light beam. Furthermore, mirror spacing for a Herriott cell needs to be tightly controlled to less than approximately ±0.016% deviation from the ideal spacing, defined by the ROC of the reflectors, to achieve the reentrant condition of the exit beam and minimal diffraction losses of the light beam at the at least one light beam injection and exit hole in the at least one reflector.

As an alternative to non-resonant optical configurations for TDL spectrometer, such as Herriott cells and the like, resonant optical cavities can also be used to achieve absorption path lengths exceeding approximately 100 meters. Such resonant optical cavities are required for cavity ring down spectroscopy (CRDS), and its derivative intra cavity output spectroscopy (ICOS). Resonant cavities require expensive feedback loops to achieve resonance with the target analyte absorption wavelength and very expensive ideal reflectors with total light losses from absorption, scattering, diffraction, refraction, transmission, wavefront distortion and the like remaining below approximately 10 ppm. These absorption spectroscopy approaches only work well in clean gas environments, which do not foul mirrors and operate in carrier gas streams with negligible sample gas absorption.

Measuring the target analyte absorption with a collimated laser beam with materially invariant beam shape may appear as an obvious solution to those skilled in the art of optical design, because propagation of a collimated laser beam defines an interaction volume and a path length of the light beam with the absorbing sample gas, which may not materially change with occurrence of absorbing layers created by condensates or by fouling from the sample gas. Furthermore, light propagation in such an optical system and manufacturing tolerances for the optical elements and their relative positioning can easily be calculated by applying well known rules for Gaussian beams, provided that optical surfaces of reflectors and transmissive elements can be fully described by mathematical formulas. This can help maintain calibration fidelity of an absorption spectrometer by not allowing material changes in absorption path length, as a result of operation and/or fouling of reflectors. A change in absorption path length may cause a material offset of the concentration reading with respect to spectrometer calibration, due to the exponential dependence of the target analyte absorption on the length of the absorption path. However, requiring an optical system of a TDL spectrometer to maintain a shape of a light beam propagating through an optical system and at least minimizing, if not eliminating loss of light from the ideal beam shape and path, through scatter, diffraction, refraction, beam shape distortion, and the like, imposes the use of expensive optical components, which have been manufactured to very tight tolerances, approaching an ideal mathematical description of all optical surfaces.

A robust sample cell that can be used in a spectrometry system in an industrial setting is described herein. The robust sample cell can be a variation of an ideal sample cell (e.g. Herriot cell, White cell), such that the beam of light passing through the analysis sample and being received by the detector is affected by loss in intensity due to light scattering, diffraction, refraction, and the like from reflector surfaces and apertures in the beam path between the light source and the detector. The variation in the robust sample cell can include one or more surfaces (e.g., reflective surfaces) that are not as optically smooth as required to meet the definition of an ideal sample cell, such as a Herriot cell or White cell. Meaningful data can be obtained using a sample cell with rough reflective surfaces by analyzing the ratio of the signal from the second-harmonic of light that passed through the gas sample to the total power of the light after passing through the gas sample. In this way, reduction in the overall intensity of the light exiting the sample cell after passing through the gas sample will not necessarily correlate to deterioration in data quality. Alternatively, the system and sample cell can use direct absorption spectroscopy (which does not generate a harmonic signal) to determine the amount of an analyte in a sample. In some such systems, a near simultaneous total light transmission assessment can be used in which the laser wavelength is shifted or zero gas runs through the system in addition to the gas sample.

The spectrometer and spectrometry system described herein can analyze gas samples to detect the presence of one or more chemical species or compounds of interest. Such chemical species or compounds can be referred to as analytes. The analytes may be the same phase as the gas sample, or the analyte may be a different phase. The analytes can absorb light at one or more frequencies, yielding a characteristic absorbance spectrum for each analyte or combination of analytes. In some implementations, the spectrometer and spectrometry system can be configured to yield concentration data for one or more analytes based upon the absorption data acquired.

Analyte compounds with which implementations of the current subject matter can be used include, all gas phase atoms, molecules, and ions, which absorb light, but are not limited to, hydrogen sulfide ($H_2S$); hydrogen chloride (HCl); water vapor ($H_2O$); hydrogen fluoride (HF); hydrogen iodide (HI); hydrogen cyanide (HCN); hydrogen bromide (HBr); ammonia ($NH_3$); arsine ($AsH_3$); phosphine ($PH_3$); oxygen ($O_2$); carbon monoxide (CO); carbon dioxide ($CO_2$); chlorine ($Cl_2$); nitrogen (N2), hydrogen (H2); hydrocarbons, including but not limited to methane ($CH_4$), ethane ($C_2H_6$), ethylene ($C_2H_4$), acetylene($C_2H_2$), methyl-acetylene, propadiene, sulfur dioxide, mercaptans, carbonyl sulfide, carbon disulfide, ethane, propane, ethylene, propylene, phosgene, and the like; fluorocarbons; chlorocarbons; alcohols; ketones; aldehydes; acids, bases and the like. The analytes can be detected within a background reference analyte that can include, for example, various fluids and/or one or more gases selected from hydrocarbons fluoro-carbons, chloro-carbons, silanes, freons, water vapor, ammonia, carbon monoxide, carbon dioxide, nitrogen, oxygen, chlorine, hydrogen, methane, ethane, propane, butane, pentane, hexane, septane, octane, nonane, decane, ethylene, propylene, butene, acetylene, vinyl-chloride, acrylonitrile, and acetonitrile.

Conventional spectrometer and spectrometry systems rely on long path lengths of the light passing through the analysis sample to obtain sensitivity of the analysis. In order for conventional spectrometer and spectrometry systems to optimize the beam path, the reflective surfaces in the sample cell reflect the beam from the light source in such a way that minimizes intensity loss due to light scattering, diffraction, refraction, and the like from reflector surfaces and apertures in the beam path between the light source and the detector, and that prevents material alteration of the beam path. Roughness in the reflective and transmissive components can cause deterioration in signal, including loss in beam intensity. Conventional spectrometer and spectrometry systems rely on absolute absorption of light by the sample from light. Conversely, the systems and methods described herein utilize absorption signals of a higher frequency with respect to the total power of the light that passes through the analysis sample.

The spectrometer and spectrometry system described herein can utilize absorbance spectroscopy. Particularly, the spectrometer can be a TDL (tunable diode laser) spectrometer. Tunable diode laser systems can employ modulation techniques. Modulation techniques can enable the TDL system to obtain spectra or data from samples at second-harmonic or higher frequencies of the modulation frequency while the spectrometry light source, that can be a laser, emits at least a portion of its light intensity at the fundamental modulation frequency.

A TDL spectroscopy system as provided herein can generate data that can be used to detect the presence and calculate the concentration of an analyte species in a sample even when only a fraction of the light passing through a sample arrives at a detector. The light arriving at the detector need only to have passed through a sample gas volume on a defined, fixed path. The fixed path is only required to have sufficient length for absorption of the light by a chosen analyte to occur when the analyte is present in an amount equal to or greater than a desired concentration level. The fixed path length can be determined by the relative position and direction of the light source aperture and the detector aperture in a TDL system. Inherently, light propagates in a straight line between a light source and a terminus (e.g., a light detector). The fixed path of a beam of light can be lengthened by at least one reflection on an arbitrary surface in a sample cell. Optionally, at least one aperture of a suitable size can be inserted into the linear fixed beam path to minimize the possible variation in path length, for example by reducing variations that can occur with multiple reflections from random surfaces within a sample cell. An aperture can include a pinhole or a spatial filter such as a hollow tube, an optical fiber, and the like. Thus, the fixed path length need not be defined by the propagation of a collimated beam of light with a defined beam shape. That is to say that the light propagating on a fixed path length can vary from a Gaussian shape in a TDL spectrometry system, and yet the system can be able to determine the concentration of a chosen analyte in a sample.

Surface fouling in an optical TDL spectrometry system, as well as replacement of reflective surfaces in such a system, can change the intensity of the light that passes through the system. This change in light intensity over time can create a concentration reading offset that differs from the calibrated values. Compensation for this reading offset can be achieved by measuring the offset against the calibrated system baseline loss by running a zero gas through the sample cell. A zero gas has no optical absorption and can include vacuum, nitrogen, hydrogen, homonuclear diatomic molecules (or analogous species for infrared light), and the like. By running a zero gas through the TDL system, the system baseline resulting from optical losses in the system can be established. Comparing the readings resulting from running a zero gas through a TDL system at the time of calibration and after surface fouling or component replacement can allow for compensating for the offset.

Another method for compensating for a reading offset in a TDL optical system after surface fouling or component replacement can include using wavelength modulation spectroscopy, including but not limited to 2f-WMS (second-harmonic wavelength modulation spectroscopy) and ratioing of the harmonic, for example 2f, signal with the total transmitted, non-resonant DC light beam signal to determine the concentration level of one or more chosen analytes. In such a compensation method, optical attenuation of the light beam from any of diffraction; scatter; refraction; and absorption by condensates, liquids, heavy molecules, and the like, does not generate a 2f signal. However, such optical attenuation diminishes the 2f and DC light signals at the same rate so that the TDL system can maintain calibration fidelity even with the fouling of reflective surface or the exchange of optical components.

Further detail regarding operating a TDL spectroscopy system and analysis of the resulting data can be found in U.S. Pat. No. 7,679,059, the entire disclosure of which is hereby incorporated by reference herein.

FIG. 1 is a process flow diagram 100 in which, at 110, a light source emits a beam into a sample volume comprising one or more analyte. Thereafter, at 120, at least one detector detects at least a portion of the beam emitted by the light source. One or more components of a spectrometry system then determine the total power of the light that has passed through the sample volume to impinge on the at least one detector, at 130. Similarly, one or more components of the spectrometry system then determine the signal from of the light generated by the light source at its second-harmonic that has passed through the sample volume to impinge on the at least one detector, as in 140. After acquiring data regarding the total power of light and the signal or date of light using the second-harmonic of the light source, at 150, one or more components of the spectrometry system identifies, and optionally quantifies, the analytes in the sample.

Figure 2:
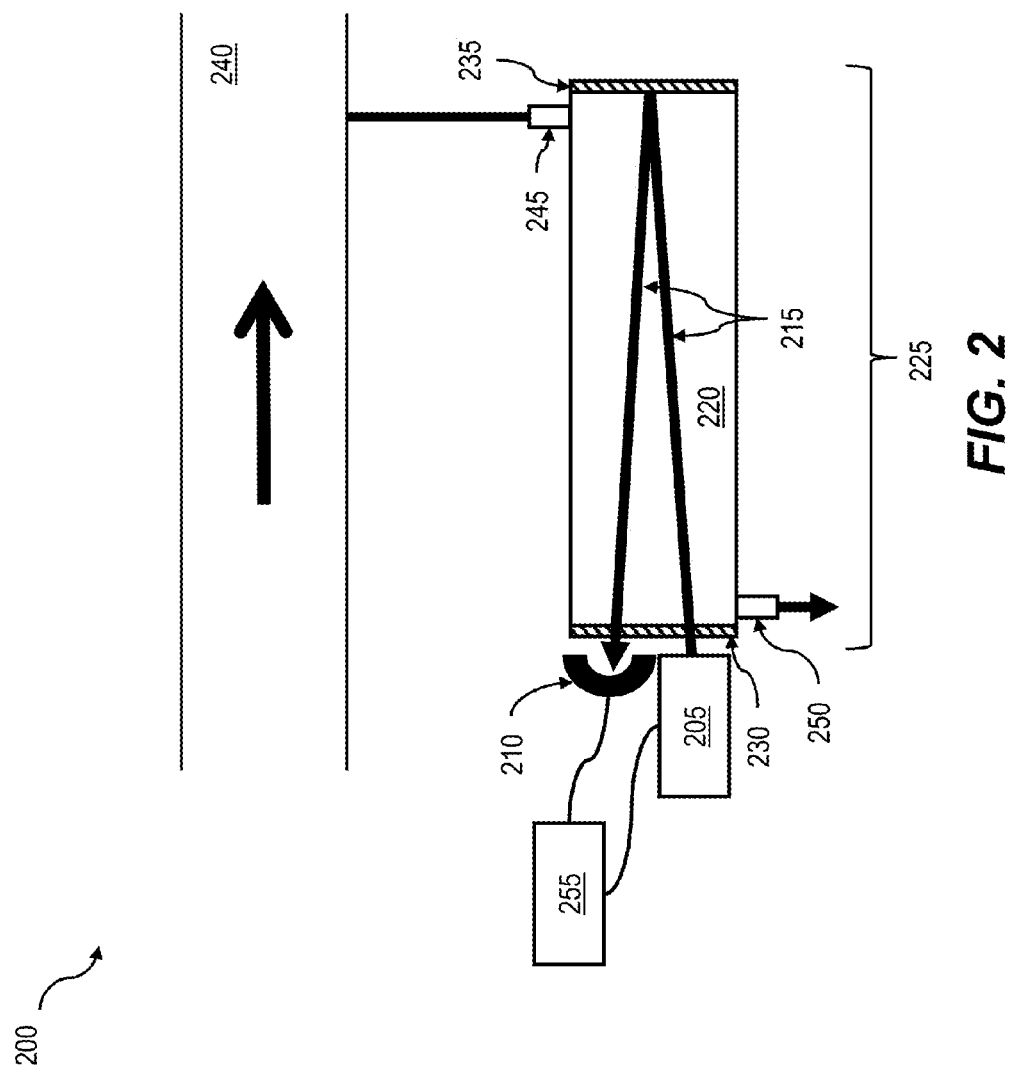
FIG. 2 is a diagram illustrating a spectrometer with a sample cell.
Figure 3:
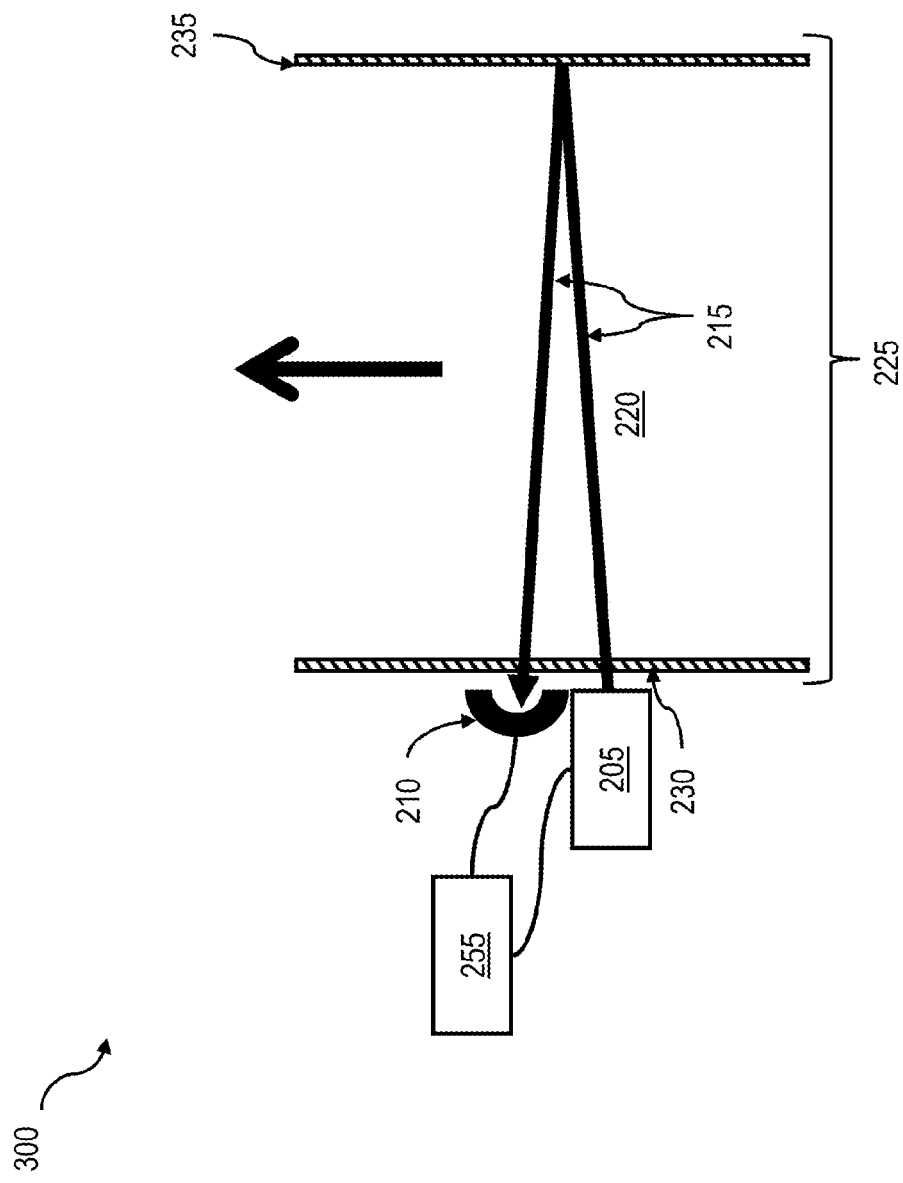
FIG. 3 is a diagram illustrating a open path spectrometer.

FIGS. 2 and 3 are diagrams 200 and 300 that show example spectrometers for implementing the current subject matter. While the following is described in connection with detecting analyte (e.g., absorbing media) within gas, it will be appreciated that the current subject matter can also be applied to detecting analyte within liquid. A light source 205 provides a continuous or pulsed light that is directed to a detector 210 via a path length 215. The light source 205 can include, for example, one or more of a tunable diode laser, a tunable semiconductor laser, a quantum cascade laser (QCL), an intra-band cascade laser (ICL), a vertical cavity surface emitting laser (VCSEL), a horizontal cavity surface emitting laser (HCSEL), a distributed feedback laser (DFB), a distributed Bragg reflector laser (DBR), a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, and the like. The detector 210 can include, for example, one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photo-multiplier, a CMOS (complementary metal oxide semiconductor) detector, a CCD (charge coupled device detector) detector and the like.

The path length 215 can traverse one or more volumes. In the example systems 200-300 shown in FIGS. 2 and 3, the path length 215 can twice traverse a volume 220 of an optical cell 225 that includes a window or other at least partially radiation transmissive surface 230 and a rough, or non-ideal, reflector (e.g., a mirror, etc.) 235 or other at least partially radiation reflective surface that at least partially defines the volume 220. Sample gas can, in some implementations, be obtained from a gas source, which in the example of FIG. 2 is a pipeline 240, for delivery to the volume 220, for example via a sample extraction port or valve 245 that receives the sample gas from the source. Gas in the volume 220 can exit via a second outlet valve or port 250.

As illustrated in FIG. 2, in some variations, the volume 220 can be part of a housing that defines a sample cell that can be, for example, a variation of one or more of a Herriott cell, an off-axis optical resonator, an on-axis optical resonator, an elliptical light collector, a toroidal closed ring reflector, a parabolic light collector, a spherical light collector, an aspherical light collector, a White cell, an optical cavity, a hollow core light guide, a multiple pass configuration in which the light beam is reflected at least once or a single pass configuration in which the light is not being reflected while the light traverses the sample cell.

In other variations, as illustrated in FIG. 3, the volume 220 can be part of an open path system that does not include a dedicated sample cell. Open path systems can be used for various applications including atmospheric pollutant studies, fence line monitoring, process line/tank leak detection, industrial gas-purity applications, explosion limit control and monitoring and control of combustion processes, especially on exhaust stacks or in burner box control.

A controller 255, which can include one or more programmable processors or the like, can communicate with one or more of the light source 205, the detector 210, and the reflector 235 for controlling the emission of the light 215 and receiving signals generated by the detector 210 that are representative of the intensity of light impinging on the detector 210 as a function of wavelength. In various implementations, the controller 255 can be a single unit that performs both of controlling the light source 205 and receiving signals from the detector 210, or it can be more than one unit across which these functions are divided. Communications between the controller 255 or controllers and the light source 205 and detector 210 can be over wired communications links, fiber-optical communications links, optical free-space communication links, wireless communications links, or any combination thereof. The controller 255 can also, in some cases, be used to quantify an amount of analyte in the sample using the signal generated by the detector 210. In other variations, the quantification can be determined by at least one remote data processor.

As described above, fouling or damage to a reflective surface in a sample cell can cause reduction in the intensity of light that reaches a detector in a spectroscopy unit after passing through a gas sample, causing the sample cell to become non-optimal, and with reflective surfaces that have an effective surface roughness that exceeds ideal conditions. It is also possible that a cell can be made (e.g. fabricated) with roughness in the reflective surfaces or with other imperfections that can decrease beam intensity. Fabricating a reflective surface to the tight tolerances required of a proper Herriott cell, White cell, or the like, is often times intensive and costly, requiring techniques that can create a surface roughness of less than 10 Angstroms and utilizing materials that can be polished, but that are often fragile. Use of such optical materials, including glasses and ceramics and the like, can furthermore present design challenges and increased cost when generally lower coefficients of thermal expansion for such materials need to be mechanically combined with metal tubing and enclosures which are commonly required in transporting flammable and environmentally incompatible gases such as hydro-carbon, fluoro-carbon, chlorocarbon, silane gases and the like. Creating a sample cell with one or more rough reflective surfaces can reduce the cost, increase the durability, and save a process from downtime needed to clean or repair an ideal sample cell.

Figure 4:
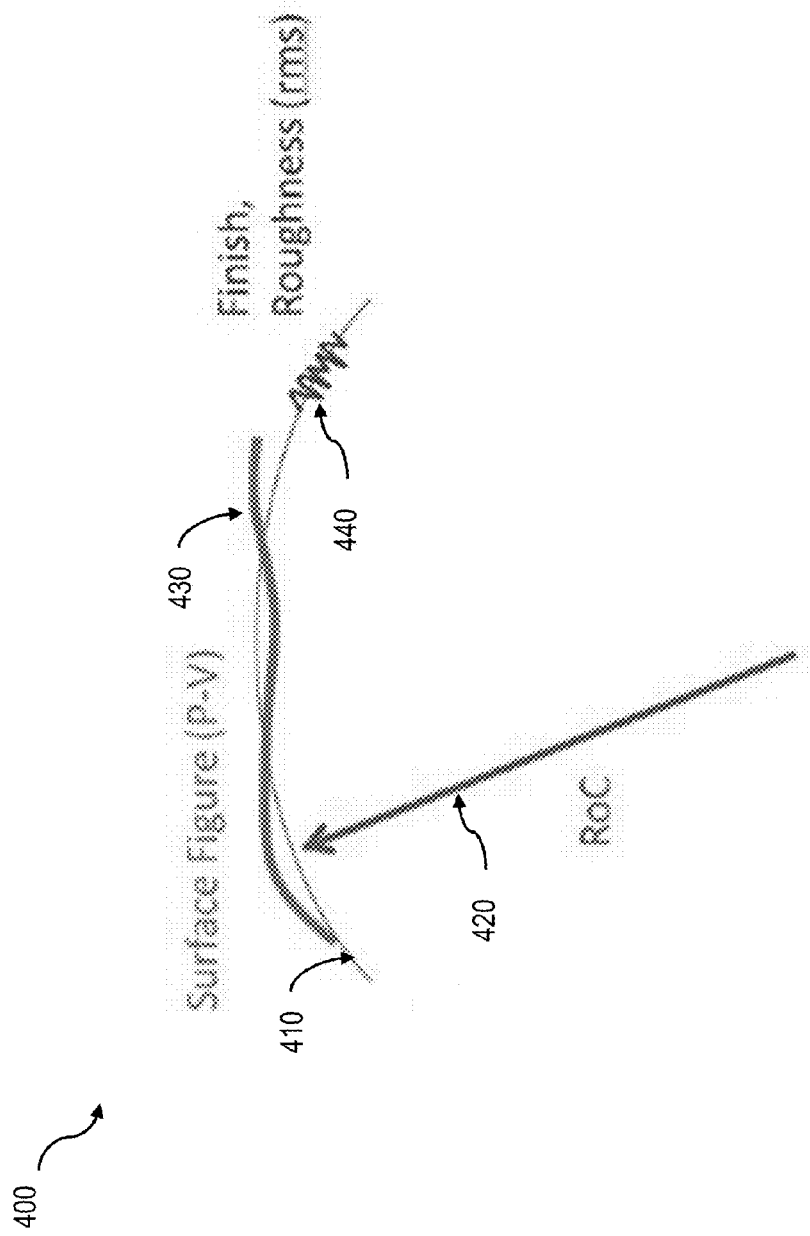
FIG. 4 is a diagram illustrating an enlarged view of an exemplary reflective surface that can be used in a spectrometer.

FIG. 4 illustrates an enlarged view 400 of an exemplary, rough, reflective surface 410 that can be used in a spectrometer. The reflective surface 410 can have one or more of: a radius of curvature (RoC) 420, a surface FIG. 430, and a finish or surface roughness 440 that vary from ideal values. The rough reflective surface 410 may yield a lower light intensity on the detector 210 versus an ideal cell, however so long as the total power of the light and a second-harmonic (2f) or higher order harmonic signal can be detected, a calculation can be made of the ratio of the signal from the light source's 2f or higher order harmonic signal to the total power of the light impinging on the detector.

In some implementations, the reflective surface 410 can be made of machined metal, etched metal, molded metal, cast metal, formed metal, a dielectric coated metal, a semiconductor-coated metal, machined plastic, etched plastic, molded plastic, cast plastic, plastic films, metal-coated plastic, dielectric-coated plastic, semiconductor-coated plastic, a composite material, metal-coated composite material, dielectric-coated composite material, semiconductor-coated composite material, a machined ceramic material, a molded ceramic material, a cast ceramic material, a pressed and sintered ceramic material, a metal coated ceramic material, a dielectric coated ceramic material, a semiconductor coated dielectric material, a machined glass material, an etched glass material, a molded glass material, a cast glass material, a metal coated glass, a dielectric coated glass material, a semiconductor coated glass material, a dielectric material, a semiconductor, a machined semiconductor, an etched semiconductor, a metal coated semiconductor, a dielectric coated semiconductor or any combination thereof. A machined metal or machined plastic reflective surface can be single-point diamond turned mirror. Single-point diamond turned surfaces (e.g., mirrors) can have artifacts and surface roughness on the order of 20 Angstroms or more. An etched semiconductor or metal or plastic or glass or ceramic reflective surface can have artifacts and surface roughness on the order of 20 Angstroms or more. Furthermore, the reflective surface 410 can be coated with at least one of at least one dielectric material, at least one metal, at least one semiconductor, at least one organic material or the like.

The rough reflective surface 410 can diffract the light beam. In some implementations, the rough reflective surface 410 can diffract the light beam in a random manner. Conversely, in some implementations, the rough reflective surface 410 can diffract the light beam in a predetermined pattern. The rough reflective surface 410 may cause scattering, diffractive, or both scattering and diffractive signal losses.

Surface roughness values of the rough reflective surface 410 can range from 20 Å RMS to 10,000 Å RMS or more, as measured by AFM (atomic force microscopy), over at least a 10 μm by 10 μm surface area. Alternately, the surface roughness can be measured with an optical interferometer of comparable resolution to an AFM. In some implementations, the rough reflective surface 410 can have areas with different surface roughness values, such that some areas are smoother than others.

The radius of curvature of a rough surface 410 can vary from ±0.05% to ±15% or more of the radius of curvature of mirrors required for an ideal Herriott cell.

The surface figure of a rough reflective surface 410 can be uniform over the area of the reflective surface. Alternatively, the surface figure can vary across the area of a rough reflective surface 410. The surface figure of a reflector is described as the peak to valley deviation of the surface from its ideal surface, which can include at least an area which is a flat surface, a spherical surface, a parabolic surface, an elliptical surface and the like. The surface figure values for a rough reflective surface can range from $\lambda/100$ to $10\lambda$, where $\lambda$ is the wavelength of the light beam. As described above, spectrometers and spectrometry systems described herein can determine useful information from a signal from a sample cell with less than optimal light beam propagation. In addition, or as an alternative to, less than optimal signal resulting from a sample cell with rough reflective surfaces or varied dimensions, the non-optimal signal can be the result of an irregular beam of light emanating from the light source. For example, the beam of light from the light source can have an irregular cross-section, can vary in intensity over the area of the cross-section of the light beam, or otherwise be variable in a less than optimal way. Use of an imperfect light source can allow for a less expensive spectroscopic analysis system, as well as one that may be more tolerant of fluctuations in ambient temperature and pressure at the light source.

As described above, a tunable diode laser (TDL) spectrometer can operate without the conditions of an ideal sample cell. That is to say that a TDL spectrometry system can operate when losses due to diffraction, refraction, and the like are greater than an optimized minimal level. A fixed beam shape, for example a Gaussian beam shape, need not be maintained while a light beam propagates through a TDL spectrometry system. The tolerance of the TDL optical system for the existence of non-ideal conditions allows for the use of non-ideal reflectors, light sources which can produce beams of light with variable beam shape, deviations from the ideal in reflector spacing, and the like. The ability of the TDL system to produce absorption data, even with a non-ideal optical set-up, including an optical system that is subject to surface fouling or component replacement without being taken off-line for calibration, allows for a TDL system that can be made and maintained with reduced cost and effort as compared to a system that utilizes an ideal sample cell.

The volume 220, shown in FIGS. 2 and 3, can be maintained at a stable temperature and pressure. Alternatively, the volume 220 can include one or more temperature and/or pressure sensors to determine a current temperature and pressure within that volume for use in one or more calculations to compensate for temperature and/or pressure changes relative to a validation or calibration condition of the spectroscopic instrument. Furthermore, the volume 220 can be adjusted to preset temperature and pressure by heating elements and pressure control elements or mass flow controllers. Knowledge of the temperature and/or pressure by the spectroscopy system can allow for more accurate analysis of the gas sample.

The controller 255, or alternatively one or more other processors that are either collocated with the other components or in communication therewith, can perform the processing functions discussed above in reference to the method illustrated in FIG. 1. Communication between the components of the controller 255 or the controller and other processors can be wired, wireless, or a combination thereof.

As noted above, it will be appreciated that the current subject matter is applicable to a wide variety of closed path and open path spectrometers. In particular, the current subject matter can be used with a wide variety of sample cells including Herriot cells, toroidal sample cells, as well as other shaped sample cells having reflective surfaces and/or adopting reflective interior portions/housings. Further, the reflectors/reflective surfaces can be flat, spherical, elliptical, convex, concave, aspherical, astigmatic or a combination of any of the foregoing.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor, a virtual free space optical display, for displaying information to the user and a keyboard and a pointing device, such as for example a mouse or a trackball or a kinetic input device, or a free space optical input device and the like, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:
a light source configured to emit a beam along a beam path through a sample volume comprising an analyte;
at least one detector positioned to detect at least a portion of the beam emitted by the light source;
at least one reflector positioned along the beam path intermediate the light source and the at least one detector, the at least one reflector having a surface roughness greater than about 20 Å RMS and less than a maximum surface roughness that prevents detection of a total power of the beam and a higher order harmonic signal of the beam by the at least one detector; and
a controller configured to perform operations comprising:
determining a ratio using the total power and the higher order signal impinging on the at least one detector, and
calculating a concentration of the analyte in the sample volume based on the ratio.

2. The apparatus of claim 1, wherein the at least one reflector is integral to a housing of a sample cell of a spectrometer that also comprises the light source and detector.

3. The apparatus of claim 1, wherein the at least one reflector is coupled to a housing of a sample cell of a spectrometer that also comprises the light source and detector.

4. The apparatus of claim 1, wherein the at least one reflector has a radius of curvature varying from a predetermined radius of curvature by more than ±0.05%, ±0.075%, ±0.1%, ±0.15%, ±0.22%, ±0.5%, ±1%, ±1.5%, or ±2%.

5. The apparatus of claim 1, wherein the predetermined radius of curvature is based on a spacing and position of the at least one reflector in relation to the at least one light source and/or at least one detector.

6. The apparatus of claim 1, wherein the at least one reflector has a radius of curvature that is infinite or substantially infinite.

7. The apparatus of claim 1, wherein at least a portion of the at least one reflector has a negative radius of curvature.

8. The apparatus of claim 1, wherein at least a portion of the at least one reflector has a positive radius of curvature.

9. The apparatus of claim 1, wherein at least a portion of the at least one reflector is cylindrical, aspheric, toroidal, spherical, parabolic or elliptical.

10. The apparatus of claim 9, wherein the at least one reflector has a surface roughness greater than 20 Å RMS, 40 Å RMS, 80 Å RMS, 100 Å RMS, 150 Å RMS, 200 Å RMS, 250 Å RMS, 500 Å RMS, or 1000 Å RMS over at least a surface area of 10 μm by 10 μm.

11. The apparatus of claim 1, wherein the at least one reflector has a surface figure greater than, in at least one area, $\lambda/100$, $\lambda/50$, $\lambda/10$, $\lambda/5$, $\lambda/2$, $\lambda$, $2\lambda$, $3\lambda$, $5\lambda$, or $10\lambda$, where $\lambda$ is a wavelength of light in the beam emitted from the light source.

12. The apparatus of claim 1, wherein the one or more reflective surfaces cause a loss of intensity of the beam from the light source to the at least one detector.

13. The apparatus of claim 12, wherein the one or more reflective surfaces randomly diffract the beam from the light source.

14. The apparatus of claim 12, wherein the one or more reflective surfaces diffract the beam from the light source in a predetermined pattern.

15. The apparatus of claim 1, wherein the one or more reflective surfaces cause scattering, diffractive, or both scattering and diffractive signal losses such that an intensity of the beam detected by the at least one detector is below a predefined percentage of an intensity of the beam as emitted by the light source, and wherein the beam of light includes a modulation frequency and the apparatus further includes a controller configured to determine a concentration of an analyte using wavelength modulation spectroscopy, the determining comprising processing intensity data from the at least one detector to demodulate the intensity data.

16. The apparatus of claim 1, wherein the one or more reflective surfaces comprise at least one of single point diamond turned mirrors, molded surfaces, wet etched surfaces, dry etched surfaces, pressed mirrors, sintered mirrors, or formed surfaces.

17. The apparatus of claim 16, wherein the one or more reflective surfaces comprise at least one of a: machined metal, etched metal, molded metal, cast metal, formed metal, a dielectric coated metal, a semiconductor-coated metal, machined plastic, etched plastic, molded plastic, cast plastic, plastic films, metal-coated plastic, dielectric-coated plastic, semiconductor-coated plastic, a composite material, metal-coated composite material, dielectric-coated composite material, semiconductor-coated composite material, a machined ceramic material, a molded ceramic material, a cast ceramic material, a pressed and sintered ceramic material, a metal coated ceramic material, a dielectric coated ceramic material, a semiconductor coated dielectric material, a machined glass material, an etched glass material, a molded glass material, a cast glass material, a metal coated glass, a dielectric coated glass material, a semiconductor coated glass material, a dielectric material, a semiconductor, a machined semiconductor, an etched semiconductor, a metal coated semiconductor, or a dielectric coated semiconductor.

18. The apparatus of claim 17, wherein the one or more reflective surfaces comprise a plastic material coated with a metal or a dielectric or a semiconductor.

19. The apparatus of claim 17, wherein the one or more reflective surfaces comprise a ceramic material coated with a metal or a dielectric or a semiconductor.

20. The apparatus of claim 17, wherein the one or more reflective surfaces comprise a semiconductor coated with a metal or a dielectric.

21. The apparatus of claim 1 further comprising:
at least one aperture included along the beam path between the light source and the at least one detector.

22. A method comprising:
emitting, by a light source forming part of a spectrometer, a beam along a beam path into a sample volume comprising an analyte;
detecting, by at least one detector, at least a portion of the beam emitted by the light source after the beam has been reflected by at least one reflector, the at least one reflector being positioned along the beam path intermediate the light source and the at least one detector and has a surface roughness greater than about 20 Å RMS and less than a maximum surface roughness that prevents detection of a total power of the beam and a higher order harmonic signal of the beam by the at least one detector, the detecting of the at least a portion of the beam comprising quantifying the total power and the higher order harmonic signal impinging on the at least one detector; and
calculating a concentration of the analyte in the sample volume based on a ratio determined using the total power and the higher order signal impinging on the at least one detector.

23. The method of claim 22, wherein the at least one reflector is integral to a housing of a sample cell of a spectrometer that also comprises the light source and detector.

24. The method of claim 22, wherein the at least one reflector is coupled to a housing of a sample cell of a spectrometer that also comprises the light source and detector.

25. The method of claim 22, wherein the at least one reflector has a radius of curvature varying from a predetermined radius of curvature by more than ±0.05%, ±0.075%, ±0.1%, ±0.15%, ±0.22%, ±0.5%, ±1%, ±1.5%, or ±2%.

26. The method of claim 22, wherein the predetermined radius of curvature is based on a spacing and position of the at least one reflector in relation to the at least one light source and/or at least one detector.

27. The method of claim 22, wherein the at least one reflector has a radius of curvature that is infinite or substantially infinite.

28. The method of claim 22, wherein at least a portion of the at least one reflector has a negative radius of curvature.

29. The method of claim 22, wherein at least a portion of the at least one reflector has a positive radius of curvature.

30. The method of claim 22, wherein at least a portion of the at least one reflector is cylindrical, aspheric, toroidal, spherical, parabolic or elliptical.

31. The method of claim 30, wherein the at least one reflector has a surface roughness greater than 20 Å RMS, 40 Å RMS, 80 Å RMS, 100 Å RMS, 150 Å RMS, 200 Å RMS, 250 Å RMS, 500 Å RMS, or 1000 Å RMS over at least a surface area of 10 μm by 10 μm.

32. The method of claim 22, wherein the at least one reflector has a surface figure greater than, in at least one area, $\lambda/100$, $\lambda/50$, $\lambda/10$, $\lambda/5$, $\lambda/2$, $\lambda$, $2\lambda$, $3\lambda$, $5\lambda$, or $10\lambda$, where $\lambda$ is a wavelength of light in the beam emitted from the light source.

33. The method of claim 22, wherein the one or more reflective surfaces cause a loss of intensity of the beam from the light source to the at least one detector.

34. The method of claim 33, wherein the one or more reflective surfaces randomly diffract the beam from the light source.

35. The method of claim 34, wherein the one or more reflective surfaces diffract the beam from the light source in a predetermined pattern.

36. The method of claim 22, wherein the one or more reflective surfaces cause scattering, diffractive, or both scattering and diffractive signal losses such that an intensity of the beam detected by the at least one detector is below a predefined percentage of an intensity of the beam as emitted by the light source, wherein the method further comprises:
controlling the light source to emit the beam of light with a modulation frequency; and
determining a concentration of an analyte using wavelength modulation spectroscopy, the determining comprising processing intensity data from the at least one detector to demodulate the intensity data.

37. The method of claim 22, wherein the one or more reflective surfaces comprise at least one of single point diamond turned mirrors, molded surfaces, wet etched surfaces, dry etched surfaces, pressed mirrors, sintered mirrors, or formed surfaces.

38. The method of claim 37, wherein the one or more reflective surfaces comprise at least one of a: machined metal, etched metal, molded metal, cast metal, formed metal, a dielectric coated metal, a semiconductor-coated metal, machined plastic, etched plastic, molded plastic, cast plastic, plastic films, metal-coated plastic, dielectric-coated plastic, semiconductor-coated plastic, a composite material, metal-coated composite material, dielectric-coated composite material, semiconductor-coated composite material, a machined ceramic material, a molded ceramic material, a cast ceramic material, a pressed and sintered ceramic material, a metal coated ceramic material, a dielectric coated ceramic material, a semiconductor coated dielectric material, a machined glass material, an etched glass material, a molded glass material, a cast glass material, a metal coated glass, a dielectric coated glass material, a semiconductor coated glass material, a dielectric material, a semiconductor, a machined semiconductor, an etched semiconductor, a metal coated semiconductor, or a dielectric coated semiconductor.

39. The method of claim 38, wherein the one or more reflective surfaces comprise a plastic material coated with a metal or a dielectric or a semiconductor.

40. The method of claim 39, wherein the one or more reflective surfaces comprise a ceramic material coated with a metal or a dielectric or a semiconductor.

41. The method of claim 39, wherein the one or more reflective surfaces comprise a semiconductor coated with a metal or a dielectric.

42. The method of claim 22, wherein the spectrometer further comprises:
at least one aperture included along the beam path between the light source and the at least one detector.

43. An apparatus comprising:
a light source configured to emit a beam along a beam path through a sample volume comprising an analyte;
at least one detector positioned to detect at least a portion of the beam emitted by the light source;
rough reflector means positioned along the beam path intermediate the light source and the at least one detector having a surface roughness greater than a predefined amount, the surface roughness of the rough reflector means being sufficient to cause scattering, diffractive, or both scattering and diffractive signal losses such that an intensity of the beam detected by the at least one detector is below a predefined percentage of an intensity of the beam as emitted by the light source, the predefined percentage being below approximately 10% of an original beam intensity; and a controller configured to perform operations comprising:
controlling the light source to emit the beam of light with a modulation frequency,
processing intensity data from the at least one detector to demodulate the intensity data, and
calculating a concentration of the analyte in the sample volume using wavelength modulation spectroscopy based on a ratio using a total power of the beam and a higher order harmonic signal of the beam impinging on the at least one detector.

* * * * *